United States Patent [19]

Detsch

[11] Patent Number: 5,015,186

[45] Date of Patent: May 14, 1991

[54] DENTAL IMPLANT ATTACHMENT SYSTEM

[76] Inventor: Steven G. Detsch, 4115 The Hill Rd., Bonita, Calif. 92002

[21] Appl. No.: 385,666

[22] Filed: Jul. 26, 1989

Related U.S. Application Data

[63] Continuation-in-part of Ser. No. 100,578, Sep. 24, 1987, Pat. No. 4,854,872.

[51] Int. Cl.$^5$ .......................... A61C 8/00; A61C 3/00
[52] U.S. Cl. ........................ 433/173; 433/8; 433/18; 433/74
[58] Field of Search ............. 433/173, 174, 175, 176, 433/74, 18, 8

[56] References Cited

U.S. PATENT DOCUMENTS

| | | | |
|---|---|---|---|
| 3,979,828 | 9/1976 | Taylor | 433/175 |
| 4,024,638 | 5/1977 | Linkow et al. | 433/176 |
| 4,238,189 | 12/1980 | Tirino | 433/74 |
| 4,443,192 | 4/1984 | Blitz | 433/74 |
| 4,746,293 | 5/1988 | Lundgren et al. | 433/173 |
| 4,756,689 | 7/1988 | Lundgren et al. | 433/173 |
| 4,863,383 | 9/1989 | Grafelmann | 433/174 |
| 4,907,969 | 3/1990 | Ward | 433/173 |

Primary Examiner—John J. Wilson
Attorney, Agent, or Firm—Michael W. York

[57] ABSTRACT

A prosthetic implant attachment system for mounting a dental prosthesis on a root implant including a base member having a lower end sized to seat on the upper end of an implant cylinder and an upper end of outer diameter substantially equal to the average outer diameters of various teeth, a securing device for securing the base member on the root implant, and various straight, angled or variable angled prosthetic heads for securing to the prosthesis. The upper end of the base member and the lower end of the prosthetic head have interengageable and indexable locking formations for preventing rotation between the parts which can be engaged in any of a number of possible relatively rotated fixed, indexed positions. A releasable securing device secures the prosthetic head to the base member. The prosthesis can be mounted on the prosthetic head by cementation, screw fixation, or other techniques. A system for preventing rotation of the base member on an implant cylinder is set forth as is an improved analogue pin that is removable from the model. An implant system with an orthodontic bracket is also described.

6 Claims, 5 Drawing Sheets

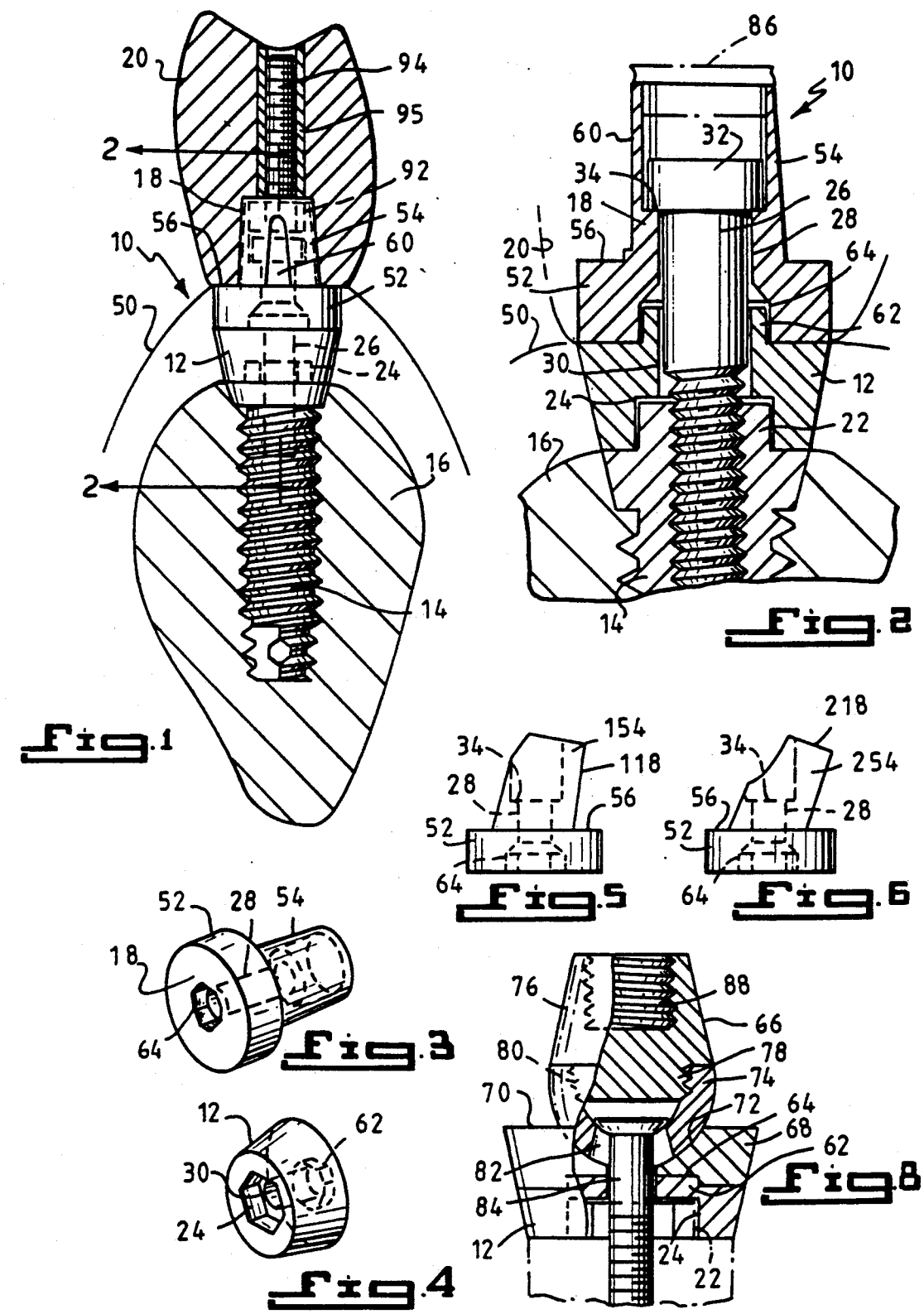

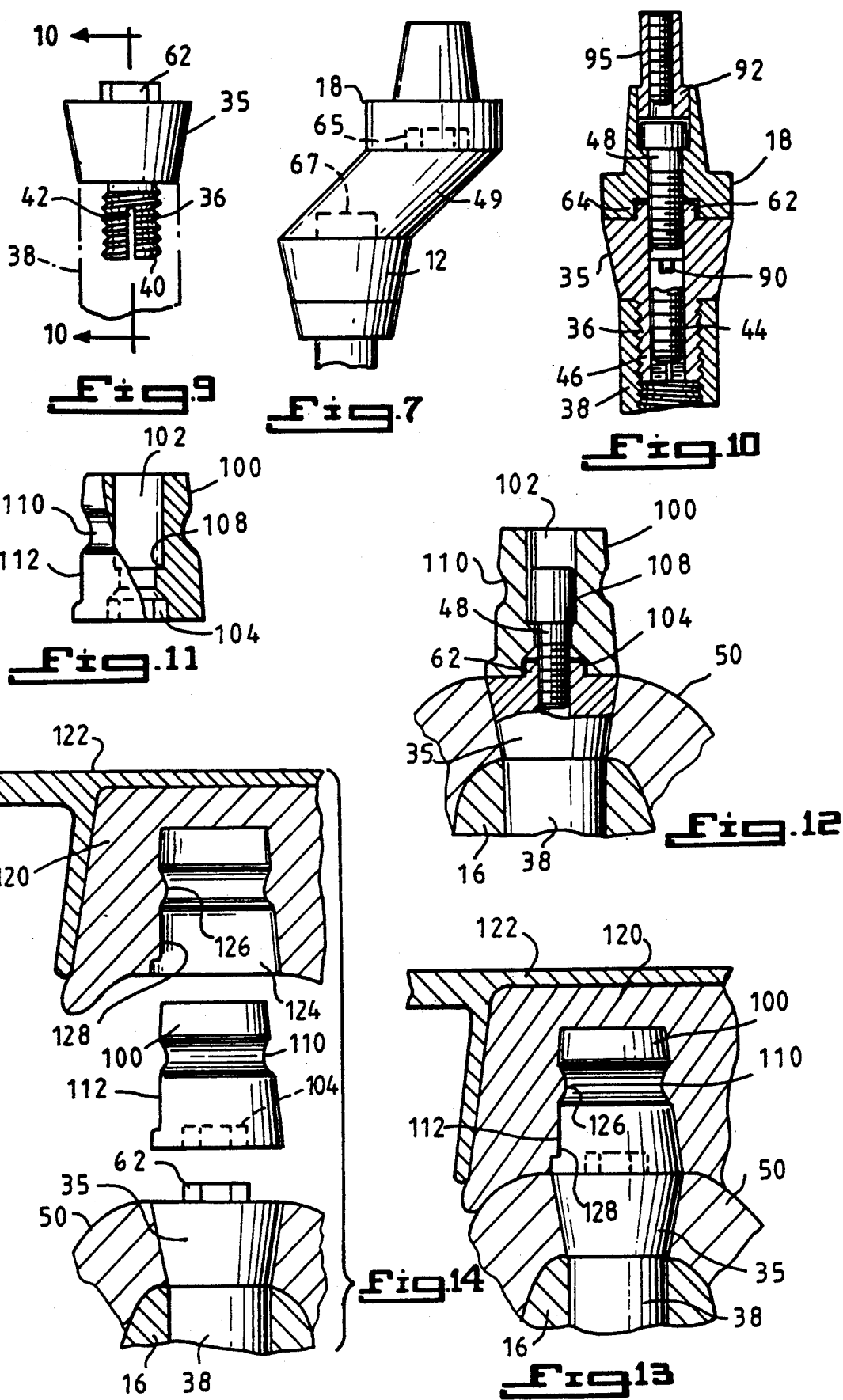

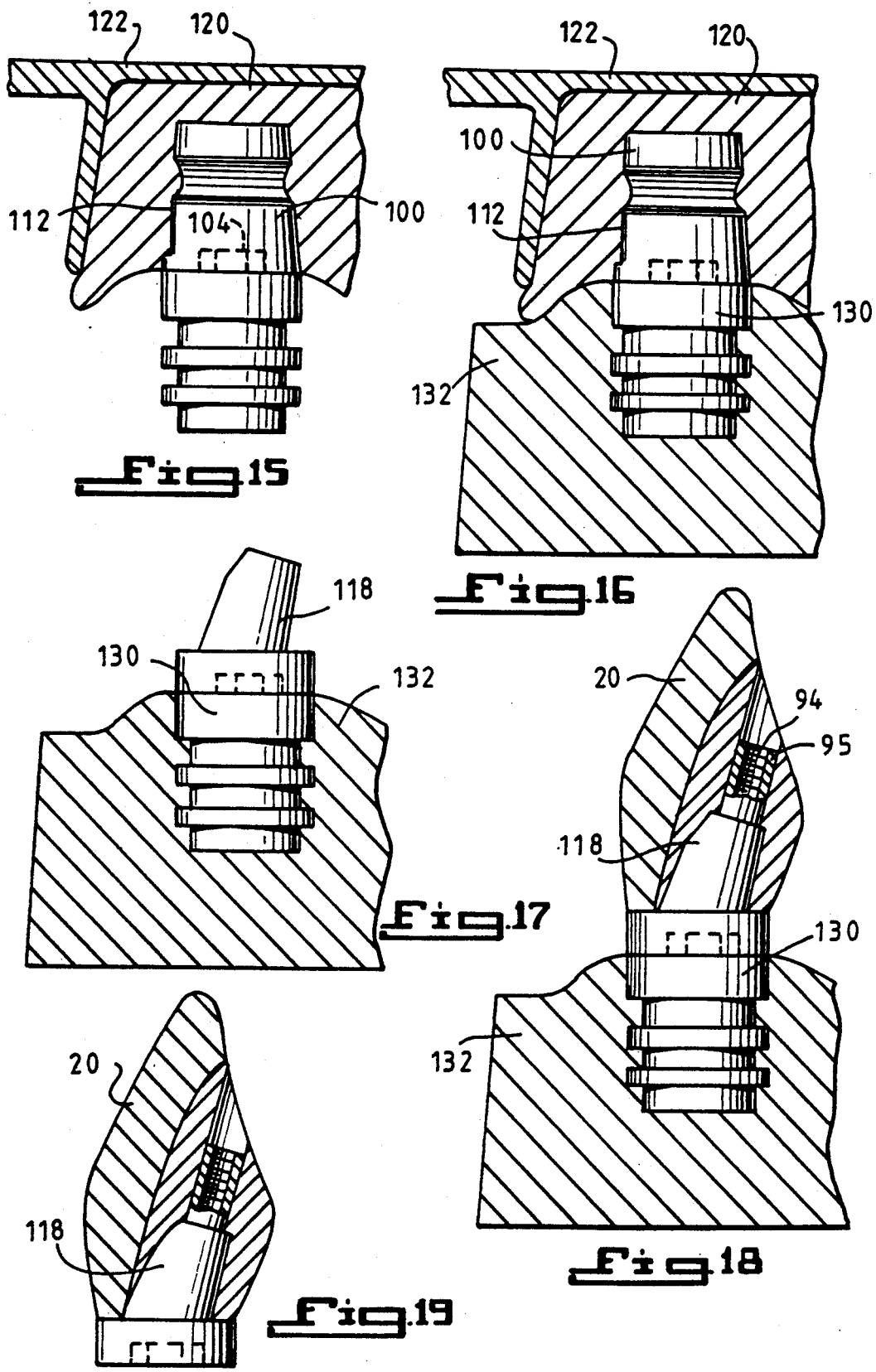

DENTAL IMPLANT ATTACHMENT SYSTEM

CROSS REFERENCE TO RELATED APPLICATION

This application is a continuation in part of pending, U.S. patent application Ser. No. 07/100,578 filed Sept. 24, 1987 now U.S. Pat. No. 4,854,872, issued 08/08/89.

BACKGROUND OF THE INVENTION

The present invention relates to a prosthetic implant attachment system and method for mounting a dental prosthesis such as a single artificial tooth or crown, a partial or full denture, or a bridge on an artificial root implant which has previously been embedded in the jaw bone in place of the natural root.

There are at present a number of different dental implant systems in use. Most systems include an artificial root portion or implant cylinder which is placed into a custom bored hole in the jaw bone. A prosthetic coronal section is attached to the artificial root portion when healing and bone integration of the artificial root portion is complete, and a dental prosthetic appliance such as a crown, denture, partial denture or bridge is attached to the coronal section. The prosthetic coronal section must pass through the connective tissue and overlying mucosa for attachment to the prosthesis. There is no interchangeability between the currently available implant systems, so that once a prosthesis has been mounted on one type of artificial root, any future replacements must use the same implant system to mount on that root. In other words, the prosthetic section of one implant system can be secured only to the artificial root of the same system. Since the average lifetime of a prosthesis is of the order of 10 years, at which time a patient may have moved or be seeing a different dentist, significant problems can arise when a replacement is needed. The dental practitioner must always have several implant systems on hand, since patients may have been fitted with various different types of implants at different times, and will also need the appropriate set of tools for mounting the various systems. This problem is likely to become more acute as the number of individuals fitted with such implant systems increases.

Another problem with existing attachment systems is that of adjusting for undesirable placement angulation of the submerged artificial root. Since the prosthetic coronal section or post normally extends coaxially from the artificial root, and the prosthesis must be mounted on this post, undesirable angulation may make it difficult to align the prosthetic tooth or teeth with the natural tooth line. This is a particular problem with front teeth, since for cosmetic reasons it is desirable that a screw or the like securing a crown or artificial tooth to the post does not exit through a front face of the tooth. Some attempts for adjusting angulation are provided in various existing systems, for example providing the post or prosthetic coronal section with a bendable neck portion, but this results in a weakened area which is liable to break. In other systems fixed angled portions are provided on the post, but this allows one angular adjustment only and thus does not allow easy adjustment or a wide range of angulation adjustment.

Another problem with replacing front teeth with existing implant systems is that the post or prosthetic section securing the artificial tooth or teeth to the implant will often be visible between the base of the tooth and the gum, particularly as the gum recedes naturally with time. This results in an unattractive gap which can be seen when the wearer smiles.

SUMMARY OF THE INVENTION

It is an object of the present invention to provide an implant attachment system which can be used to secure a prosthesis to any artificial root implant cylinder.

According to the present invention, a dental implant attachment system for mounting a dental prosthesis on an artificial root implant comprises a base member having a lower end sized to seat on the upper end of the root implant cylinder and an upper end having an outer diameter substantially equal to that of a tooth for mounting on the implant, and a prosthetic head having a lower end for mounting on the upper end of the base member and an upper end for securing to a dental prosthesis. A securing assembly is provided to secure the base member to the implant cylinder and the prosthetic head to the base member.

Preferably, a series of different base members and prosthetic heads are provided in an attachment kit, with a number of different prosthetic heads in the kit being attachable to each of the base members. The base members include members sized to seat on any existing artificial implant cylinder, and members having upper ends of diameter equivalent to a variety of average natural tooth sizes, for example in the range from 3.5 mm to 7.0 mm. The prosthetic heads have lower end cuff portions sized to seat on the upper end of each of the base members with no overlap, and each have an upwardly projecting post portion preferably of tapering conical shape. The prosthetic heads include post portions at angles between 0 and 30 degrees to the cuff portion, to allow for angulation adjustment. Alternatively, a variable angle prosthetic head may be provided which comprises an annular member and a post section with a swivel engagement with the annular member to allow the post section to be swiveled into a desired angle relative to the base member axis before locking it in the desired position.

The prosthetic heads preferably include a 0.5–2 mm wide butt joint which allows for a thickness of metal and ceramic to be placed between the post portion and the edge of the base portion. This section may be customized or shaped as desired to further improve cosmetics by following gingival form.

Any suitable securing devices such as screw fasteners may be provided for securing the selected base member to the implant cylinder and for securing the selected prosthetic head to the base member. The upper end of the base member and lower end of each prosthetic head include interengageable indexing formations for securing the prosthetic head against rotation on the base member in any one of a series of fixed, indexed positions. Thus the angled prosthetic heads can be rotated through 360 degrees relative to the base member to select the indexed position providing the best possible angulation before locking the head to the base member. In one arrangement the interengageable formations comprise corresponding male and female configurations each having flats around their outer diameter. The male and female configurations may, for example, comprise hexagon or octagon nut and bore formations. With an octagonal locking formations, the prosthetic head can be engaged in any one of eight possible different angular indexed orientations relative to the base member. The interengageable locking formations for providing the fixed, indexed positions may alternatively comprise a series of teeth, grooves or serrations, for example.

The interengageable formations will prevent rotation between any of the prosthetic heads and the base member to which they are attached, reducing the risk of loosening of the attachment structure as a result of dental forces, and also allow rotation of the angled heads into any one of a plurality of different possible fixed, indexed positions to adjust for the optimum orientation of the angled heads in the jaw. The fixed orientation of interengageable locking formation of the base member when mounted in the jaw establishes an indexing position for orientation of the finished prosthesis made in the laboratory. Thus the prosthesis can be precisely positioned on to the base member in the mouth.

In an alternative embodiment, the prosthetic head includes an annular member having a concave indent for seating a convex end element of the post portion. The post portion can be swiveled relative to the concave indent to adjust the angle of the prosthetic head post as desired. This embodiment also rests upon and is orientated to a base member by an interengageable locking formation. A suitable fastener is provided for locking the seat element in the desired orientation.

Thus, in order to mount any type of prosthesis on any artificial root implant cylinder, the base member having the appropriate lower and upper end dimensions is selected. This member is suitably mounted and secured to the implant cylinder. An impression head is then fastened to the base member, and impression is taken. The impression head is removed and may be replaced with a healing cap or with a temporary crown form. An analog of the base member is then fastened to the impression head and the analog and impression head are inserted into the impression. A cast is then made, into which the analog is set at the appropriate orientation. The impression head is removed, and the cast model of the patient's jaw with the embedded analog is used in a laboratory on a dental surveyor to orient an appropriate prosthetic head, either with a straight, angled or swivelling post section for increased adjustability. The selected prosthetic head is mounted on the base member analog at the optimum angular orientation. An appropriate wax pattern is crafted by those skilled in the art to exactly fit the prosthetic head. The prosthetic cast is then made from the wax pattern, and the parts are disassembled. The dentist can then reassemble the parts, mounting the prosthetic head on the base member in the patient's jaw and then cementing or otherwise attaching the prosthesis to the prosthetic head.

The indexing locking formations between the prosthetic head and base member allows indexing between clinical and laboratory work and also allows for correction of undesired placement angulation of the submerged implant cylinder by choice of suitable angled prosthetic heads. They also effectively make the attachment structure into a single fixed unit since the separate parts cannot rotate relative to one another once they are secured together. Thus the prosthetic and artificial root implant are effectively joined together by means of a single fixed unit and will be more secure.

The sizing of the base member to that of natural teeth improves the appearance of the attachment, particularly if the outer surface of the base member is covered with a suitable tooth colored ceramic. Although a prosthesis such as a crown would originally extend down slightly below the crest of the gum line around the implant, the gum may recede with time and thus the base member or transmucosal element may become visible. However, when the base member is of equivalent size to the crown and is tooth colored, this ceases to be a significant cosmetic problem. Alternately, one can make use of the inherent interchangeability of the system and duly elect a new shorter base member to replace the original member.

Preferably, the prosthetic head cuff portion is of larger diameter than the post portion to leave an annular rim or "waxing butt joint", providing for fabrication of a thicker and thus mechanically stronger layer of ceramic in the prosthetic crown or bridge. This thickness also allows for more predictable ceramic color customization. The rim is suitably in the range of 0.5 to 3 mm in width, depending on the tooth size. The post portion is preferably conical, and may have suitable rotation resisting formations on its outer surface to resist rotation of the prosthesis on the prosthetic head. These formations may comprise opposed flats or grooves, for example. Such formations are less critical in the prosthetic heads having angled post portions, which will inherently resist rotation.

The prosthetic head cuff portion annular rim area is made of adequate thickness or depth to allow customized reshaping of the rim by those skilled in the art to approximate the exact shape of the gingival cuff, thus allowing optimal cosmetic prosthetics for anterior teeth to be achieved.

The prosthesis is cemented or otherwise attached to the prosthetic head. The prosthesis is preferably removable by means of a retrieval element fashioned into the prosthesis which allows the prosthesis to be removed from the prosthetic head. This element consists of an all threaded screw within a threaded tube cast into the prosthesis above the prosthetic head. It may be used in two fashions. Once cemented, the prosthesis may be separated from the prosthetic head by turning the screw which pushes down on the underlying head and breaks the cement seal. In an alternative arrangement, a longer screw is threaded through the tube and into an expansion module fitted into the recess at the top of the straight prosthetic head. Turning the screw tightens the expansion module against the walls of the recess and secures the crown without cement. Turning the screw in the opposite direction releases the prosthesis.

In the event of extreme bony resorption of the alveolar ridges, extension sections may be inserted between the base member and the prosthetic head to accomodate the interalveolar distance. These sections are made to varying appropriate lengths and have matching interengageable formations to the base elements and prosthetic heads and are thus connected in the manner previously described to these elements.

BRIEF DESCRIPTION OF THE DRAWINGS

The present invention will be better understood from the following detailed description of some preferred embodiments, taken in conjunction with the accompanying drawings, in which like reference numerals refer to like parts, and in which:

FIG. 1 is a side elevation view showing one version of the dental implant attachment system according to the invention in place securing a prosthesis to an artificial root implant embedded in a jaw bone;

FIG. 2 is an enlarged sectional view taken on the line 2—2 of FIG. 1;

FIG. 3 is a perspective view of a first type of head element for use in the system shown in FIG. 1;

FIG. 4 is a perspective view of a first type of base element for use in the system shown in FIG. 1;

FIG. 5 is a side elevation view of an alternative, inclined head element;

FIG. 6 is a side elevation view of another inclined head element;

FIG. 7 is a side elevation view of an alternative, offset head element;

FIG. 8 is a side elevation view, with portions cut away, of a base and adjustable head element according to an alternative embodiment;

FIG. 9 is a side elevation view of an alternative base element according to the invention with an expandable portion for attachment to an artificial root implant cylinder;

FIG. 10 is a sectional view taken on line 10—10 of FIG. 9, showing the base element of FIG. 9 attached to an implant cylinder and assembled with one of the possible head elements for mounting a prosthesis;

FIG. 11 is a side elevation view, partially cut away, of an impression head element for use in taking an impression of the location and orientation of a base element mounted on an implant cylinder;

FIGS. 12 to 19 show successive stages in a method of intraoral impression taking, transfer to a dental laboratory in a stone mounting, fabrication of a custom prosthesis and mounting a dental prosthesis in the jaw using the attachment systems of FIGS. 1 to 10;

DESCRIPTION OF THE PREFERRED EMBODIMENTS

Figure 20:
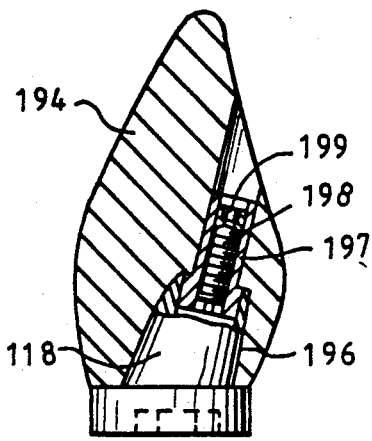
FIG. 20 is a side elevation view, partially in section, showing an example of an incisor temporary crown for use with the attachment system of this invention.

The dental implant attachment system shown in the drawings is designed to allow a prosthesis to be mounted on any existing implant cylinder or artificial root. The attachment system 10 when in place as shown in FIGS. 1 and 2 comprises several basic parts, including a base member 12 designed to seat on the upper end of an implant cylinder 14 embedded in the jawbone 16, and a prosthetic head or post 18 designed to seat on the upper end of member 12 and to form a mounting for seating a prosthesis such as a crown 20 or other prosthetic device.

A first fastener or securing device is provided for securing the base member 12 to the implant cylinder 14. The fastener may be of any suitable type depending on the internal configuration of the implant cylinder. In the version shown in FIGS. 1 and 2, the implant cylinder is of a type having internal screw threads and a hexagonal projection 22 at its upper end for interengagement with the appropriate connecting part. Thus, in the embodiment of FIG. 1, the base member 12 has a corresponding hexagonal indent 24, as best shown in FIG. 4, for mating engagement with projection 22 to secure the base member against rotation.

In the version of the system shown in FIGS. 1 and 2, the base member is secured to the implant cylinder and the head element 18 is secured to the base member by the same fastener device, a single headed screw fastener 26 which projects through an axial bore 28 in the head 18, through an aligned axial bore 30 in base member 12, and into the screw-threaded bore in the implant cylinder. The dimensions of the screw threaded end of the fastener 26 correspond to those of the screw threaded bore in cylinder 16. The head 32 at the upper end of fastener 26 seats on an internal shoulder 34 in head bore 28.

FIGS. 9 and 10 show an alternative fastener arrangement for securing the attachment system to the implant cylinder. In this arrangement a second type of base member 35 is provided, which has an expansion fastener 36 projecting from its lower end and dimensioned to fit closely into the bore of implant cylinder 38, which may have internal screw threads as shown or alternative configurations. The fastener has fingers 40 separated by slits 42 at its lower end. A headed expansion screw 44 is designed to extend through axial bore 46 in base member 36 and into a threaded bore in expansion fastener 35 to urge fingers 40 outwardly into gripping engagement with the implant cylinder bore. The fastener may have screw threads or other formations on its outer surface for improved gripping engagement with the implant cylinder bore. The expansion fastener dimensions are chosen according to the dimensions of the implant cylinder bore to which it is to be attached, and different diameter expansion fasteners may be provided on different base members for attaching to different types of implant cylinders. The expansion fastener will restrict rotation of the base member relative to the implant cylinder as well as axial movement of the base member out of the cylinder.

The same prosthetic heads 18 can be secured to a base member 12 of the type shown in FIGS. 1, 2 and 4 or the base member 35 with an expansion fastener projection as shown in FIGS. 9 and 10. Thus, the appropriate base member can be selected according to the type of implant cylinder to which the prosthesis is to be secured. In practice any appropriate type of fastener for securing the base member to the implant cylinder may be provided, which both restricts rotation of the base member and also movement of the base member out of the cylinder. The expansion fastener of FIGS. 9 and 10 provides a positive but reversible lock to the walls of the artificial root recess. Permanent retention may be achieved, if desired, by cementing the fastener into the recess.

In the embodiment of FIGS. 9 and 10, the head is secured to the base member by means of an additional screw fastener 48 which extends through bore 28 in the head 18 and into a screw threaded bore at the upper end of base member 35. Thus the base member in FIGS. 9 and 10 is provided with a screw threaded configuration at its upper end sized to receive screw fastener 48, and a counterbore at its lower end with a screw threaded configuration for receiving the expansion screw.

In the embodiment of FIGS. 1, 2 and 4 and in the embodiment of FIGS. 9 and 10, the lower end of the base member is of diameter corresponding to the external diameter of the upper end of the implant cylinder on which it is to be seated, so that there is no overlap for ingress of bacteria or the like. The upper end of the base member is of diameter substantially corresponding to the average tooth diameter of the tooth which is to be mounted on the implant. Thus the base member may be a straight cylinder, but is more likely to be of inverted frusto-conical shape as shown in FIGS. 1, 2, 4, 9 and 10 with the diameter of the lower end being less than that of the upper end. The external diameter averages of natural teeth generally range between 3 and 7 mm (Black's anatomical tooth averages) and preferably a range of base members is provided with upper diameters in this range, for example 3.5 mm, 5 mm and 7 mm, and with lower diameters for fitting all standard implant cylinders. Thus the lower diameter of the base members may range from about 2.8 mm to 7 mm, but may be outside these dimensions in some cases. Base members of varying height will also be provided, to allow for varying gingival thicknesses and natural recession of the gingiva. For example, base members of three or more different heights may be provided, such as 2 mm, 3 mm and 4 mm.

The base member 12 or 35 is designed to extend from the top of the implant cylinder embedded in the jawbone through the overlying gingiva 50 as shown in FIG. 1 for attachment to a prosthetic head. Preferably, a series of different straight and angled prosthetic heads of appropriate dimensions for fitting the various base members is provided. FIGS. 3, 5 and 6 show three different prosthetic heads 18, 118 and 218. Each head 18, 118 and 218 is of the same basic shape, comprising an annular cuff portion 52 designed to seat on the upper end of the base member and a post portion 54, 154 and 254 projecting upwardly from the cuff portion. In head 18 the post portion 54 is straight, or at 0 degrees to the head axis. In the head 118 shown in FIG. 5 the post portion 154 is angled at about 10 degrees to the head axis, and head 218 shown in FIG. 6 has a post portion 254 angled at about 20 degrees to the head axis. The prosthesis 20, which may comprise a crown or other dental prosthetic device, can be cemented or otherwise attached over the straight head 18 as indicated in FIG. 1, or over either of the angled heads shown in FIGS. 5 and 6.

Extension sections of an additional 2 mm, 3 mm and 4 mm may further be inserted between the base member and prosthetic head to accomodate excessive interalveolar distance created by extreme alveolar ridge atrophy. These sections may be straight or may be angled to allow offset extension of the prosthetic heads. FIG. 7 shows an angled extension 49 secured between base member 12 and prosthetic head 18.

The cuff portion 52 of each prosthetic head has an external diameter corresponding to that of the upper end of the selected head member, so that it sits on the head member with no overlap which could form a site for bacteria growth. It may be a straight cylinder as shown, or may have a tapered outer surface. The post portion 54, 154 and 254 of each head is preferably of tapering, frusto-conical formation as shown in FIGS. 1 to 3, 5 and 6 and of smaller dimensions than the cuff portion to leave an annular rim 56 forming a waxing butt joint providing for creation of a thicker, stronger and more cosmetic ceramo-metal prosthesis. The thickness of the annular rim to the base section is designed to allow custom recontouring of the rim to match gingiva cuff form.

Preferably a number of different straight and angled heads are provided with lower ends dimensioned for fitting the upper end of each available base member. More than two different angled heads may be provided, with angles varying between 0 and 30 degrees to the cuff portion. The straight head of FIG. 3 and the angled heads of FIGS. 5 and 6 secure to the selected base member in an equivalent manner. Like reference numerals have therefore been used where appropriate. The inclined heads shown in FIGS. 5 and 6 allow adjustment of the angulation of the implant cylinder, as explained in more detail below.

The post portion is preferably provided with suitable resistance formations to resist rotation of the attached crown or other prosthesis 20 relative to the head. In the embodiment shown in FIGS. 1 and 2, the resistance formations comprise opposed flats 60 on opposite side faces of the post portion. The provision of resistance formations is more critical in the straight head version of FIG. 3 than with the inclined heads of FIGS. 5 and 6, where the angled post portions will themselves inherently resist rotation of the secured crown.

Suitable interengageable formations are provided between the upper end of the base member and the lower end of the head to allow the head to be locked in any one of a plurality of fixed, indexed positions relative to the base member and to prevent relative rotation between the head and base member which could result from dental forces. In the embodiments shown in FIGS. 1 to 6, 9 and 10, the interengageable formations comprise corresponding male and female configurations 62, 64 at the upper end of the base member and the lower end of the head, respectively. The extension section 49 of FIG. 7 will have corresponding male and female configurations 65, 67 at its upper and lower ends, respectively for connection to the selected prosthetic head and base. The configurations in the preferred embodiment shown comprise a male and female configuration each having an octagonal outer surface, but clearly alternative formations may be used, for example hexagonal or other multifaceted forms as well as ribs, teeth, star shapes, serrations, grooves and other formations. Also, the male formation may be provided on the head and the female on the base, if desired.

Figure 22:
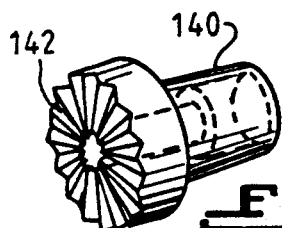
FIGS. 22 to 32 show various examples of alternative interengaging formations for adjustably locking the prosthetic head to the base member in various angular positions.
Figure 23:
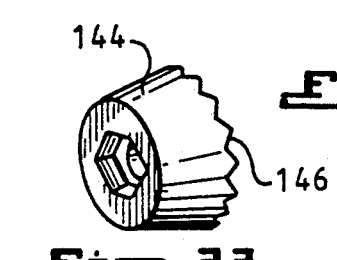

FIGS. 22 to 32 show various possible alternative formations for adjustably interlocking the head to the base. In FIGS. 22 and 23, for example, the prosthetic head 140 has a sawtooth or grooved pattern 142 on its lower end face, while the base member 144 has a corresponding, interengageable tooth pattern 146 on its upper end face. The head and base member are otherwise the same as shown in FIGS. 3 and 4. Clearly several angled heads may be provided with the same tooth pattern for engagement with base member 144. The teeth on head 140 and base member 144 will engage to allow the head to be locked against rotation in any one of a plurality of fixed, indexed positions relative to the base member.

Figure 25:
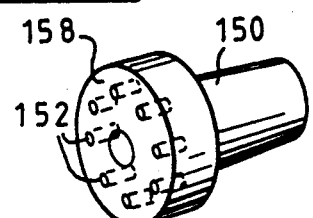
Figure 24:
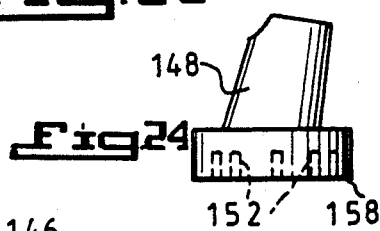
Figure 26:
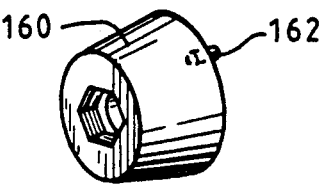

FIGS. 24 to 26 show another alternative interlocking formation. As shown in FIGS. 24 and 25, angled or straight prosthetic heads 148, 150, respectively, are provided with a series of holes or blind lines 152 in their lower end faces 158. The holes are arranged in a circular array, as can be seen in FIG. 25. The base member 160 has one or more pins 162 projecting from its lower end face (see FIG. 26) for selective engagement in one or more of the vores in the end face of the selected prosthetic head. This arrangement also allows the head to be locked against rotation in any one of a number of fixed angular positions relative to the base member.

Figure 27:
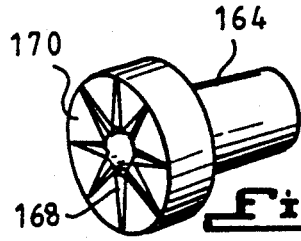
Figure 29:
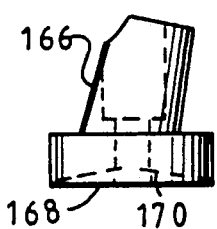
Figure 28:
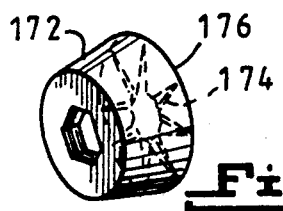

Another alternative is shown in FIGS. 27 to 29. In this version the straight and angled prosthetic heads 164 (FIG. 27) and 166 (FIG. 29) each have a star-shaped, indented formation 168 in their end face 170 while the base member 172 (FIG. 28) has a corresponding star-shaped projection 174 in its end face 176. The indented and projecting formations interengage in a plurality of fixed, indexed positions to lock the prosthetic head against rotation on the base member.

Figure 30:
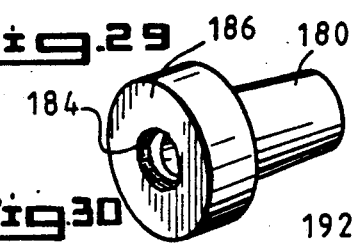
Figure 31:
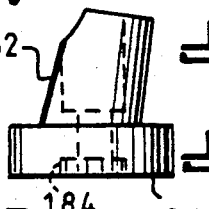
Figure 32:
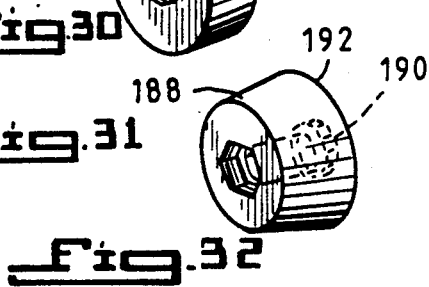

FIGS. 30 to 32 show yet another alternative in which the straight and angled prosthetic heads 180 (FIG. 30) and 182 (FIG. 31) each has an indentical, multi-sided or polygonal indent 184 in its lower end face 186 while the base member 188 has a corresponding polygonal projection 190 from upper end fase 192. This is similar to the version shown in FIGS. 3 to 6, except that the polygonal formations 184, 190 have a greater number of facets or flats. In practice any desired number of flats or sides may be provided in the polygonal formations, with the number of sides determining the number of different, fixed indexed positions of the prosthetic head relative to the base member.

The prosthetic heads and base members of FIGS. 22 to 32 are otherwise the same as those shown in FIGS. 3 to 6 and are secured together in an equivalent manner.

In the embodiment shown in FIGS. 1 to 6, the head may be locked against rotation in any one of eight possible different angular positions relative to the base member. Thus, with the angled versions of the head shown in FIGS. 5 and 6, the head can be rotated relative to the base until the optimum orientation for the angled post is located, at which point the female octagon 64 on the head can be mated with the male octagon on the base member to lock the head against rotation out of that optimum position. This allows for correction of undesirable placement of the submerged root implant cylinder, for example.

Once the head and base member are interlocked via formations 62 and 64, relative rotation is prevented and thus the parts cannot become loose as a result of inadvertent unscrewing of the fastener screw or screws. The head and base member act as a single fixed unit when secured together, and the prosthetic and implant cylinder are securely joined together by this fixed unit. Thus the risk of loosening of the prosthetic fixture as a result of dental forces during normal use is reduced. Extension section 49 of FIG. 7 may be secured to the base and prosthetic head with fastener screws in a similar fashion.

FIG. 8 of the drawings shows an alternative version of the head for allowing a greater degree of angle adjustment. In this version of the post 76 of the head 66 has a swivelling attachment to the cuff portion 68. The base member 12 is the same as that shown in FIG. 4, and the cuff portion has a female interengaging configuration 64 at its lower end for interengagement with the male configuration 62 at the upper end of the base member. The lower end of the base member in FIG. 8 may be the same as that shown in FIGS. 1, 2 and 4 or as shown in FIGS. 8 and 9, and its external dimensions are chosen in the same way.

The cuff portion of head 66 has a conical indent 72 in its upper end face 70. The post has a hollow, convex seat portion 74 for seating in concave indent 72, and a post or head portion 76 which has a screw threaded projection 78 for securing it in corresponding internal screw threads 80 in the seat portion. The seat portion 74 has a through bore 82 at its lower end through which headed fastener screw 84 projects to secure the prosthetic head seat portion to both the cuff portion 64 and the base member 12 and to secure the base member to the implant cylinder bore, as described above in connection with FIGS. 1 and 2. Alternatively, screw 84 may simply secure the seat portion and cuff portion to the base member, with an expansion fastener and screw securing the base member to the implant cylinder as in FIGS. 9 and 10.

The dimensions of bore 82 are larger than those of screw 84, as seen in FIG. 8, so that the seat portion 74 can be swivelled when the screw is loosened. The seat portion 74 is swivelled into different angular orientations relative to the cuff portion until the optimum angulation is found. Preferably, the dimensions of bore 82 allow the post portion to be tilted up to about 20 degrees relative to the cuff portion and it can be rotated through 360 degrees around the cuff portion indent to determine the optimum orientation. Thus, rather than providing several different heads at different fixed angles, as in FIGS. 1 to 6, a single swivelling head can be provided as shown in FIG. 7 to provide a greater degree of angulation adjustment.

The convex portion and concave indent may have cooperating star-shaped or ther interengageable formations for improved locking engagement when the selected angular orientation is achieved.

In the version shown in FIG. 8, the base member will first be mounted on the implant cylinder. The cuff portion 68 will then be mounted on the base member via interengaging formations 62, 64. Seat portion 74 will then be loosely secured in the cuff portion indent, and swivelled and tilted until the optimum orientation is located. At this point the screw will be tightened to lock the seat in the selected orientation, and the post portion will be screwed into the seat portion to secure the parts together. The post portion in FIG. 8 may also be provided with suitable resistance formations such as opposed flats as in FIG. 1 to resist rotation of the prosthesis on the post.

Since the upper ends of the prosthetic heads in FIGS. 1 to 6, 9 and 10 are open to receive a suitable fastener, a cementation cap 86 may be provided for mounting over the open end of the head before cementing or otherwise attaching a prosthesis to the head, as shown in FIG. 2. The cap suitably comprises a short cylindrical shaft with a short flat head which slips into and down flush with the upper end of the prosthetic head, for use when a crown, bridge or other prosthesis is to be cemented onto the head. a Alternatively, as indicated in FIG. 8, a female threaded recess 88 may be provided to accept various standard locking systems for securing custom crowns to posts, such as a simple screw. A screw having a head containing a spherical snap-lock indent for a snap-in anchor type attachment as described in U.S. Pat. No. 3,787,975 of Zuest may be provided for fitting in the upper end of the prosthetic head. Alternatively, a specialized prosthetic head may be provided with a recess for receiving a snap-lock attachment of this type directly, which may be used as a transitional attachment between removeable and fixed prosthetics, for example. Another type of base member may also be provided with a spherical snap-in recess for receiving a snap-in anchor attachment, for example.

FIG. 1 shows an alternative arrangement including a disengaging or retrieval means for dismounting a prosthesis from the assembly. The retrieval means consists of an expansion module 92 inserted into the upper end recess of the head and an "all-thread" screw member 94 within a threaded tube 95 cast into the prosthesis 20.

Turning screw 94 in a first direction tightens the expansion module 92 against the walls of the recess and secures the crown without cement. When the screw is turned in the opposite direction, the expansion module loosens and the prosthesis is released.

In an alternative, the separation or retrieval system may simply comprise an "all-thread" screw in a threaded tube cast in the prosthesis above the top of the prosthetic head. Once cemented, the prosthesis may be separated from the prosthetic head by turning the screw, pushing down on the head or cementation cap and breaking the cement seal.

In each case, the upper end of the screw 94 will be provided with a suitable slot or the like for receiving a screwdriver, or preferably with a hexagonal indent for receiving an Allen wrench for rotating the screw.

Each of the fastener screws securing the base member and prosthesis head together, either the single screw fastener of FIGS. 1 and 2 or the two fastener screws of FIGS. 9 and 10, are provided with suitable configurations on the upper face of their heads for receiving a tool for tightening and loosening the screws as desired. Instead of the standard screwdriver slots, the screw heads are preferably provided with hexagonal indents 90, one of which can be seen in the expansion fastener screw of FIG. 10, for example, for receiving the hexagonal end of an Allen wrench of suitable dimensions for tightening or loosening the screw. This allows for easy positive engagement between the tool and the screw head, unlike a standard slot for receiving a screw driver which can sometimes be difficult to locate and may become scored, particularly in small scale parts of this nature.

The parts of the attachment system described above will all be made of a suitable metal such as titanium. However, parts which may be exposed may be coated with a suitable tooth colored ceramic for cosmetic purposes. Thus the base external surface may be ceramic coated.

The attachment system is preferably provided in the form of a kit containing base members of various heights, tapers and upper and lower end diameters, and with different fastener devices for securing the various base members to root implant cylinders of various standard types and dimensions, and prosthetic heads of various dimensions and angles, as well as swivelling heads, for mounting on the selected base members, along with the appropriate screw fasteners for securing the base members to the implant cylinders and the heads to the base members. The kit also preferably includes tools for tightening and loosening the screw fasteners, as well as other specialized parts for use in dental laboratory work, as described in more detail below.

The method of attaching a prosthesis to any artificial root cylinder using the attachment system described above will now be explained in more detail, with reference to FIGS. 12 to 18. It may be used to attach a replacement prosthesis to an existing artificial root implant which has been embedded in the jawbone for some time, or to attach a new prosthesis to a recently embedded root implant cylinder.

In each case the upper end of the implant cylinder must first be exposed. In the first case the existing prosthesis and attachment system is simply removed. In the second case, the artificial root implant cylinder will be embedded in the jawbone, covered by a healing cap, and left for 3 to 6 months to allow healing and osseointegration (integration of the implant with the jaw bone) to take place in the standard manner. The upper end of the implant cylinder is then exposed using a tissue punch or the like, and the healing cap is removed using a special screwdriver. The implant area will be carefully inspected, cleaned and dried and a base member with a fastener designed for connection to that particular implant cylinder will be selected, having the appropriate height, upper and lower end dimensions, according to the gingival thickness of the patient, the tooth size, and the dimensions of the upper end of the implant cylinder.

The selected base member is then secured to the implant cylinder. In the case of the base member as shown in FIGS. 1, 2 and 4, the hexagonal indent at the lower end of the base member is seated over the corresponding hexagonal projection at the upper end of the implant cylinder. In the case of a base member 35 with an expansion fastener, as shown in FIGS. 9 and 10, the expansion fastener is screwed or fitted into the implant cylinder bore and the expansion screw is then tightened to lock the base member in place, as indicated in FIG. 12. In each of these cases it is necessary to index the prosthesis to be made with the orientation of the octagonal locking formation of the base member in the mouth. This orientation will be fixed by the hexagonal formation at the upper end of the implant cylinder with the first version of the base member, while with the second version the base member must be fixed in the implant cylinder to determine the orientation.

In the case of a base member with an expansion fastener, as shown in FIGS. 9 and 10, the expansion fastener is inserted into the implant cylinder and the expansion screw is then tightened with the appropriate tool to expand the fastener into locking engagement with the implant cylinder bore. An X-ray is taken to ensure that the base member is completely fastened down and secure, with no gap between the upper end of the implant cylinder and lower end of the base member which could allow bacteria ingress. In the case of a base member of the type shown in FIG. 4, the hexagonal indent or nut is simply engaged over the corresponding hexagonal projection at the upper end of the implant cylinder.

At this point an impression head 100 as shown in FIG. 11 is mounted on the base member, as shown in FIG. 12. The impression head 100 allows an impression to be taken of the position and orientation of the base member in the jaw, and also allows the location of the octagon lock on the base member to be indexed for laboratory work. As shown in FIG. 11, the impression head comprises a generally frusto-conical member having a through bore 102 with an octagonal indent or nut formation 104 at its lower end. An internal shoulder 108 is provided for seating of a fastener screw head. The impression head bore is therefore of similar configuration to that of the prosthetic head.

The impression head has an annular groove 110 on its outer surface for horizontal indexing, and at least one vertical flat 112 for indexing of the octagon lock orientation.

The impression head is seated on the base member with its octagonal indent 104 engaged on the octagonal projection of the base member as shown in FIG. 12. The impression head is then secured in place using either screw 26 in the case of the base member shown in FIGS. 1, 2 and 4 or the screw 48 in the case of the base member shown in FIGS. 9 and 10.

An impression is then taken of the position of the impression head, using a hydrocolloid or other dental impression material 120 supported in holder 122, as indicated in FIG. 13. The impression is removed, and the impression head is unscrewed and removed as shown in FIG. 14. In the case of the base member of FIG. 4, the base member is also removed from the implant and a healing cap is placed over the open end of the implant. In the case of the base member of FIGS. 9 and 10, a healing cap is placed over the open end of the base member, which is left in the mouth while the prosthesis is being made in the laboratory to preserve the orientation of the octagon lock. Alternatively, for optimum cosmetics, a temporary prosthesis may be mounted on the base member during this time utilizing the swivelling prosthetic head of FIG. 8.

Figure 21:
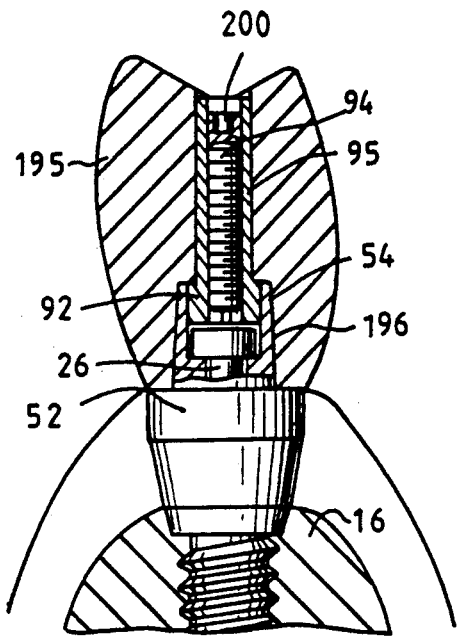
FIG. 21 is a side elevation view similar to FIG. 1 showing an example of a bicuspid temperary crown.

FIGS. 20 and 21 illustrate two acrylic temporary crown forms 194, 195, which may suitably form part of an attachment bit according to an embodiment of the invention. FIG. 20 shows an incisor form 194, while FIG. 21 shows a standard bicuspid form 195.

Each temporary crown form is made with a recess 196 in its lower end face for receiving either a straight prosthetic head as shown in FIG. 21 or an angled head as shown in FIG. 20. The head is orientated and secured to the base member as desired, and a selected, tooth colored temprary crown is engaged over the head and cemented to it. The temporary crown may be retrived after use or when replacement is necessary. A similar retrieval system to that described above may be provided.

In FIG. 20, the retrieval system comprises a threaded tube 197 cast into the temporary crown and leading into recess 196. An all-thread screw 198 engages in tube 197 and suitably has a hexagonal indent 199 in its upper end face. In order to separate the crown 194 from the head, the screw 198 is screwed down against the upper end of the head to lift the crown away from the head.

In FIG. 21, a retrieval system similar to that shown in FIG. 1 is used, and like reference numerals have been used where appropriate. Expansion module 92 is inserted in the upper end of prosthetic head. Threaded tube 95 cast into the crown 195 leads into recess 196, and all-thread screw member 94 engages within tube 95. The screw 94 preferably has a hexagonal indent 200 in its upper end face for receiving a tool such as an Allen wrench. In this version, turning screw 94 in a first direction tightens the expansion module to lock with the prosthetic head, securing the temporary corwn in place without cement. Rotation in the opposite direction loosens the expansion module to release the crown.

The temporary corwn may be used for cosmetic purposes while the permanent custom crown is made in the dental laboratory, or may be used as a permanent, low cost restorative for those who cannot afford custom crowns. The temporary crowns may be used as burnout patterns for custom ceramic crowns. They may also be modified with Duralay or ther suitable plastics materials and cutdown for use in standard ceramo-metal crown fabrication at a time savings to the dental laboratory over traditional waxing techniques.

Returning now to the description of the method of using the attachment system, the impression in FIG. 14 will have an indent 124 corresponding in shape, position and orientation to the position of the impression head in the jaw, and the indent will have indexing marks 126, 128 corresponding to the positions of the annular groove 110 and the flat 112, respectively, on the impression head.

An analogue or copy 130 of the base member, which may be of brass, is then fastened to the impression head with its octagonal projection engaging the octagonal indent of the impression head, and the impression head is then inserted back into the indent 124 in the impression, as shown in FIG. 15, using the indexing marks left by the annular groove and flat to ensure the impression head is correctly orientated. A cast using dental stone 132 is then poured into the impression, as shown in FIG. 16. The projecting base member analogue 130 will be set in the stone when it hardens. Once the cast is set, the impression head is unscrewed and removed, leaving a model of the jaw in which the base member analogue is positioned and orientated exactly as the base member is orientated in the patient's mouth. Thus the location of the octagon lock on the base member analogue will be exactly equivalent to that of the octagon lock on the base member in the mouth, allowing accurate lab work to be done in angular positioning of the prosthetic head and molding of the prosthesis.

The stone model is placed on a surveyor and various straight and angled prosthetic heads are mounted on the base member analogue to determine the optimum angulation for mounting the prosthesis so that it will be aligned with existing teeth or along a long axis where prosthetic teeth would optimally be placed. In FIG. 17 an angled prosthetic head 118 is shown mounted on the analogue in the cast. In the case of visible anterior teeth, the angulation can be adjusted so that the prosthetic head axis exits through a rear face of the tooth. Where a screw attachment is used between the prosthesis and head, the attachment screw must pass through an outer face of the tooth, with the screw opening subsequently being filled with dental plastic resin. However, with the appropriate angulation of the prosthetic head, it is possible to ensure that the screw passes more optimally through the rear face of the tooth, leaving the front, visible face smooth and continuous.

Once the appropriate head and angulation is chosen, for example by rotating an angled head relative to the analog into the optimum position for locking onto the analog octagon projection, the head is secured to the analog. The cuff or shoulder portion of the head may be customized to the gingival or gum contour, for example by cutting or grinding its upper edge into a generally concave line to follow the natural gum line in the patient's mouth. In some cases more than one tooth will be replaced at one time, in which case the above procedure is followed using several implants at different sites in the mouth.

At this point a cast of the prosthesis 20 is made. The prosthesis may comprise a single replacement tooth or crown, a bridge, a prosthetic bar, or a partial or full denture. Prior to making the cast a cementation cap is placed over the open end of the or each prosthetic head, and a suitable separation device such as a set screw consisting of an all thread in a threaded tube is placed on the prosthetic head for separation of the crown or prosthesis after casting. The casting is checked and the occlusion surfaces may be adjusted appropriately.

The parts are then disassembled in the laboratory (FIG. 19) and returned to the dentist for mounting in the mouth. A line or mark may be made on the prosthetic head for indexing to the base member in the mouth. The dentist reassembles the prosthetic head onto the base member in the mouth at the appropriate angle after removing the healing screw. The head is then secured to the base member with the appropriate screw fastener, and the cementation cap is positioned over the open end of the head. The prosthesis is then cemented or otherwise attached to the head in the usual fashion.

If the prosthesis is to be removed, the internal set screw 94 is exposed and screwed down against the cementation cap to break the cement seal and separate the prosthesis off the prosthetic head.

The method described above will also be followed in the case of the swivelling prosthetic head of FIG. 8, which allows indexing between the base member in the mouth and the analog for lab work. A dental cast with the location of the base member in the mouth will be made as described above, and the prosthetic head will be swivelled into the optimum position in the laboratory before making the prosthesis. This position will be indexed in the prosthesis itself to allow the dentist to recover the position on reassembly in the patient's mouth.

The attachment system and method described above may also be used on existing natural roots as well as on artificial roots as described above. The base member will be secured into a root canal in the manner described above, and cemented into position before attaching the prosthetic head and overlying crown or build-up.

This attachment system allows a single kit to be provided with all the parts necessary for mounting a prosthesis on any type of existing root implant. Thus the trained dental practitioner only needs to have one attachment system which can be adapted to all currently used artificial root systems. The attachment system fastens the prosthesis securely while resisting rotation, avoiding or reducing the problem of inadvertent unscrewing or unfastening if dental contact forces are applied to the coronal portion of the prosthetic head in a direction which unscrews the prosthetic head of the implant.

The base member is adjusted to the natural tooth external dimensions, so that an unattractive gap is not left when the gum line recedes naturally. The base member can be tooth colored, so that it will not be visible as a metallic line on gum recession. Thus the attachment system of this invention is generally less expensive than the case where two or more different and non-interchangeable attachment systems and associated tools must be purchased for each of the available implant systems. It provides more flexibility, allowing easy conversion from custom to non-custom crowns, or from removeable to fixed applicances and vice versa. Patients also will benefit from the reduced costs of practitioners needing only a single, standardized system and also will not suffer as the result of having an implant system fail after several years and finding that their local dentist does not use that particular system or that the local laboratories are unfamiliar with working with that system.

Figure 33:
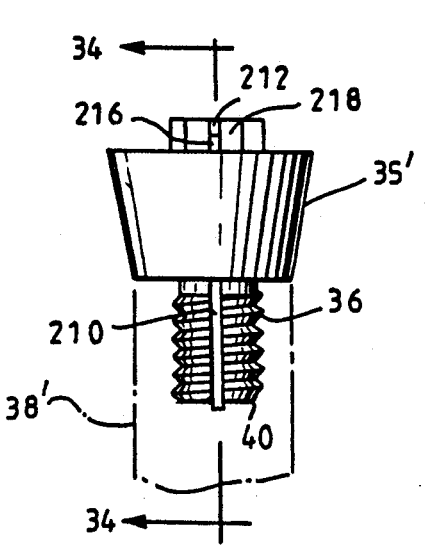
FIG. 33 is a side elevational view of an improvement to the base element illustrated in FIG. 9.
Figure 34:
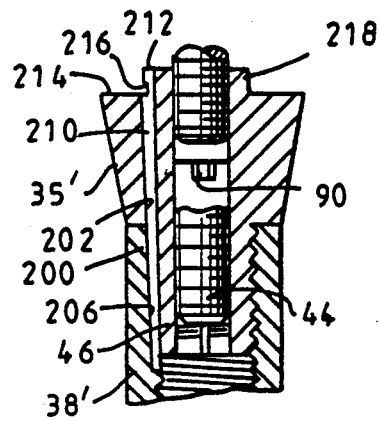
FIG. 34 is a sectional view taken substantially on the line 34—34 of FIG. 33, showing show the base element or member is secured in position.

FIGS. 33 and 34 illustate an improvement to the base member 35/implant cylinder 38 connection illustated in and previously described with respect to FIGS. 9 and 10. The problem with the base member 35 of FIGS. 9 and 10 that is screwed into the internally threaded implant cylinder 38 is that the base member 35 can work loose from the implant cylinder 38 unless the base member 35 is secured to other implants or teeth in the mouth. This limits the usefulness of the base emmber 35 and cylinder 38 system illustrated in FIGS. 9 and 10. There is a significant need and desire for single tooth implant replacement, but the system set forth in and previously described with respect to FIGS. 9 and 10 does not permit such single tooth replacement.

However, with the improved base member 35' and implant cylinder 38' connection set forth in FIGS. 33 and 34 such single tooth implant replacement is easily and effectively accomplished. The base member 35' and associated implant cylinder 38' have means for preventing rotation of the base member 35' in the implant cylinder 38' that is designated generally by the number 200. The rotation preventing means 200 comprises a hole 202 extending downward through the enlarged head portion 204 of the base member 35' that is located to coincide with a similar size hole 206 located in the implant cylinder 38' and the adjacent threaded portion 208 of the base member 35'.

The rotation preventing means 200 also comprises a generally cylindrical shaped pin member 200 that is sized and shaped to fit into and be received by these holes 202 and 206. It will be noted that this pin member 210 has a head portion 212 that extends above the upper flat surface 214 of the base member 35'. This head portion 212 has a notch 216 in its outer surface that is used to exert an upward force by a suitable tool (not shown) to remove the pin member 210 from the holes 202 and 206 when it is desired to remove the base member 35' from the implant cylinder 38'.

In order to install the rotation preventing means 200, the base member 35' is securely threaded into the implant cylinder 38'. Then, the holes 202 and 206 are drilled by using a suitable drill (not shown) by drilling downward through the base member 35' at a point adjacent its hexagonal shaped upper projection 218. Except as previously noted with respect to the rotation preventing means 200, the base member 35' and the implant cylinder 38' are substantially identical to the previously described base member 35 and implant cylinder 38. In the preferred embodiment the pin member 210 is made from stainless steel.

Figure 35:
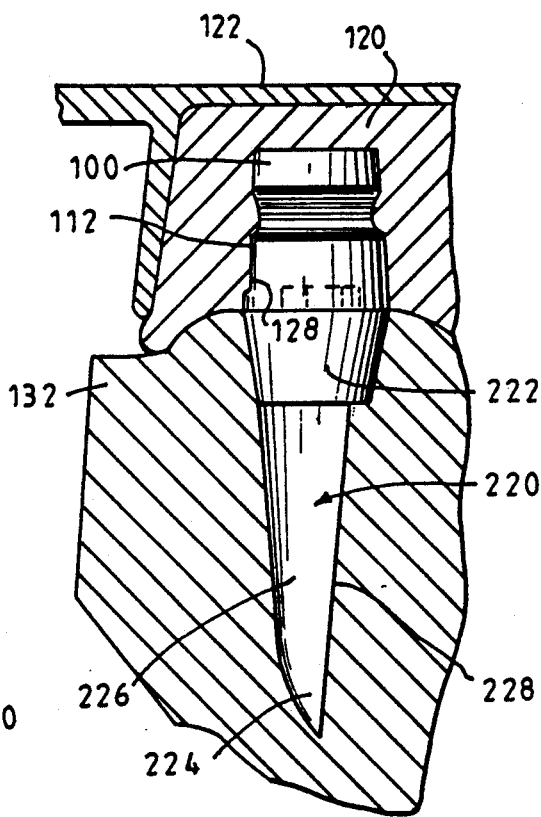
FIG. 35 is a side elevational view of an implant analog pin to replace the base member analog illustrated in FIGS. 15 through 18.

FIG. 35 illustrates an improved implant analogue pin designated generally by the number 220 that replaces the base member analogue 130 that is set forth in FIGS. 15 through 18 that has been previously described in detail. One problem with such previously used implant analoges such as the base member analogue 130 is that they are relatively short, heavy and bulky and this caused a problem during impression pouring when the mold is being vibrated to make the dental stone 132 flow readily into the details of the mold due to loosening of the transfer coping from the mold and the resultant inaccurate analogue placement in the resultant mold. Another problem with such base member analogues as the analogue 130 is that they are designed to be fixed firmly in the stone models. Consequently, the crown margins of the custom crowns made to fit to the analog margins could not be instrumented on the model or checked for accuracy.

The improved implant analogue pin 220 solves both of these problems. Because it is less bulky it has less of an inertia to cause it to dislodge the transfer coping and because it is relatively long it may be secured by standard methods (not shown) to the sides of the mold. Also as illustrated the pin 220 tapers generally from its upper intergal enlarged end portion 222 that is sized and shaped to correspond substantially to the size and shape of the previously described members 35 and 35' to its lower end portion 224 and it has generally smooth side walls 226. This allows the pin 220 to be removed from the stone 132 provided it was lubricated prior to pouring the stone 132. Also, as illustrated one side of the pin 220 has a substantially flat surface 228 that is inclined or slopes inward toward the lower end portion 22 of the pin 220. This allows the pin 220 to index itself into the model. Since the pin 220 can be removed from the mold, this permits the precise waxing of crown margins, precise application of ceramic and close examination of margin accuracy of the attached prosthetic pieces during all stages of custom implant crown fabrication.

Figure 37:
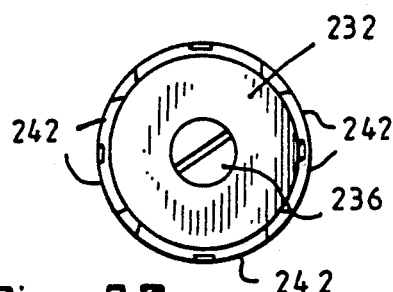
FIG. 37 is a top plan view of the orthodontic prosthetic head illustrated in FIG. 36.
Figure 36:
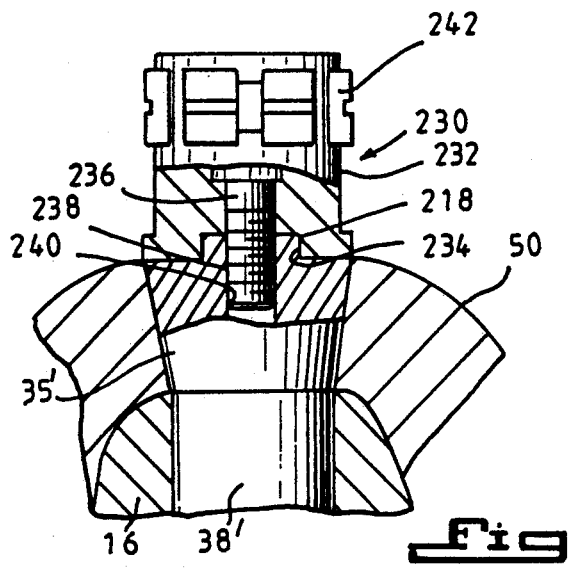
FIG. 36 is a side elevational view of an orthodontic prosthetic head for use with the base members of FIGS. 1 and 2 and FIGS. 9, 10 and 12.

FIGS. 36 and 37 illustate an orthodontic prosthetic head designated generally by the number 230 that comprises a generally cylindrical orthodontic mounting member 232 with a hexagonal shaped recess 234 on its lower end for receiving the corresponding hexagonal projection 218 on the base member 35' that is secured to the implant cylinder 38' as previously described in detail. The cylindrical member 232 is secured to the base member 35' by the screw 236 that has its threaded portion 238 threaded into the threaded hole 240 in the base member 35'. The orthodontic prosthetic head 230 also comprises an orthodontic bracket 242 located around the outer upper end portion 244 of the cylindrical member 232 that is known to those skilled in the art. Because implants fuse with bone, the implants can be used as an anchorage for applying orthodontic forces on crooked teeth when posterior or back teeth cannot be used due to their absence or due to bone loss adjacent the back teeth. It should be noted that although the base member 35' and implant cylinder 38' are shown in use with the orthodontic prosthetic head 230 other implant systems may also be used such as the base member 35 and cylinder 38 or other systems. After the base member 35', member 232 and the attached orthodontic bracket 242 and implant cylinder 38' are secured to the jaw bone 16 in the mouth, orthodontic appliances (not shown) are connected to the orthodontic bracket 242 to exert orthodontic forces on the implant cylinder 38' and adjacent jaw bone 16.

Although some preferred embodiments of the invention have been described above by way of example only, it will be understood by those skilled in the field that modifications may be made to the disclosed embodiments without departing from the scope of the invention with is defined by the appended claims.

What is claimed is:

1. A prosthetic implant attachment system for mounting a prosthetic device to the jaw bone in the mouth comprising a base member, securing means associated with said base member for permitting said base member to be secured to the jaw bone in said mouth, said base member and said securing means having threaded portions for permitting said base member to be threadably connected to said securing means, and means for preventing rotational movement between said base member and said securing means, said means for preventing rotational movement between said base member and said securing means comprising a hole in the threaded portion of said base member, a hole in the threaded portion of said securing means and a pin member locatable in the holes in the threaded portion of said base member and the threaded portion of said securing means for engaging said base member and said securing means after said base member has been threadably connected to said securing means.

2. The prosthetic implant attachment system of claim 1 wherein said pin member has a head portion with a notch for use in removing said pin member from the holes in the threaded portion of said base member and the threaded portion of said securing member.

3. An implant analogue system for use in forming an artificial tooth for a dental implant comprising an impression head and a tapered pin member having a lower end portion and having an integral enlarged head portion sized and shaped to substantially correspond to said impression head and tapering generally from the integral enlarged head portion to the lower end portion with a substantially flat inclined surface located on a portion of the tapering portion of said pin member with the inclined surface sloping inward toward the lower end portion of said pin member.

4. The implant analogue system of claim 3 wherein said impression head has a flat exterior surface portion.

5. The implant analogue system of claim 3 wherein said impression head has a groove on its outer surface.

6. An orthodontic prosthetic system for use with a dental implant secured in the jaw bone in the mouth comprising a cylindrical base member, means for securing said base member to said implant in the mouth, an orthodontic mounting member secured to said base member and an orthodontic bracket connected to said orthodontic mounting member, said orthodontic bracket having a plurality of projecting portions.

* * * * *